(12) United States Patent
Kuo et al.

(10) Patent No.: US 12,014,813 B2
(45) Date of Patent: Jun. 18, 2024

(54) CONTOURING SYSTEM

(71) Applicant: Quanta Computer Inc., Taoyuan (TW)

(72) Inventors: Kuei-Hong Kuo, Taoyuan (TW);
Yi-Ting Peng, Taoyuan (TW);
Ching-Chung Kao, Taoyuan (TW);
Ai-Ling Hsu, Taoyuan (TW); Yu-Ren Yang, Taoyuan (TW); Pei-Wei Shueng, Taoyuan (TW); Chun-You Chen, Taoyuan (TW); Kuan-Chieh Huang, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 481 days.

(21) Appl. No.: 17/361,718

(22) Filed: Jun. 29, 2021

(65) Prior Publication Data

US 2022/0148711 A1 May 12, 2022

(30) Foreign Application Priority Data

Nov. 6, 2020 (TW) .................. 109138746

(51) Int. Cl.
*G16H 30/20* (2018.01)
*G06T 7/00* (2017.01)
*G16H 30/40* (2018.01)

(52) U.S. Cl.
CPC .......... *G16H 30/20* (2018.01); *G06T 7/0012* (2013.01); *G16H 30/40* (2018.01); *G06T 2207/10081* (2013.01); *G06T 2207/20084* (2013.01)

(58) Field of Classification Search
CPC ........ G16H 30/20; G16H 30/40; G16H 20/40; G16H 50/20; G16H 50/70; G06T 7/0012;
(Continued)

(56) References Cited

U.S. PATENT DOCUMENTS 11,756,209 B2    9/2023 Lu
11,769,254 B2    9/2023 Song et al.
(Continued)

FOREIGN PATENT DOCUMENTS

CN    107403201 A    11/2017
CN    109378043 A    2/2019
(Continued)

OTHER PUBLICATIONS

Chinese language office action dated Dec. 8, 2021, issued in application No. TW 109138746.
(Continued)

*Primary Examiner* — Lewis G West
(74) *Attorney, Agent, or Firm* — McClure, Qualey & Rodack, LLP (57) ABSTRACT

Systems with a contouring method are provided for contouring one or more targets that correspond to specific organs and/or tumors in a three-dimensional medical image of a patient using neural networks. The contouring system includes a storage unit, a processing unit, and a plurality of modules that are computer operable. The processing unit is used to obtain the image, and then to generate one or more contouring images using a contouring method. The contouring method includes enhancing image features and improving contouring accuracy using an image preprocessing module, and extracting a plurality of multi-scale image representations and expanding these representations to one or more contouring images using a neural network-based contouring module.

8 Claims, 6 Drawing Sheets

(58) Field of Classification Search
CPC . G06T 2207/10081; G06T 2207/20084; G06T 2207/30016; G06T 2207/30096; G06T 7/12; G06T 7/194; G06T 2207/10088; G06T 2207/20081
See application file for complete search history.

(56) References Cited

U.S. PATENT DOCUMENTS

| | | | | |
|---|---|---|---|---|
| 11,832,982 | B2* | 12/2023 | Min | A61B 8/14 |
| 2013/0083993 | A1* | 4/2013 | Sutou | G06T 7/97 |
| | | | | 382/154 |
| 2015/0050650 | A1* | 2/2015 | Seppo | C12Q 1/6816 |
| | | | | 435/7.1 |
| 2018/0045535 | A1* | 2/2018 | Kim | G08G 1/205 |
| 2019/0156481 | A1* | 5/2019 | Sekiguchi | G06T 7/0014 |
| 2020/0143084 | A1* | 5/2020 | Rosenberg | H04L 63/0428 |
| 2020/0258235 | A1* | 8/2020 | Lu | G16H 30/40 |
| 2021/0052157 | A1* | 2/2021 | Wilson | G16H 50/20 |
| 2021/0343023 | A1 | 11/2021 | Lu | |
| 2021/0391040 | A1* | 12/2021 | Dormer | G16H 50/20 |
| 2022/0207748 | A1* | 6/2022 | Pham | G06T 5/002 |
| 2023/0329909 | A1* | 10/2023 | Morely | A61F 9/008 |
| 2023/0384117 | A1* | 11/2023 | Margin | G01C 21/3815 |

FOREIGN PATENT DOCUMENTS

| | | |
|---|---|---|
| CN | 109671053 A | 4/2019 |
| TW | 202040585 A | 11/2020 |

OTHER PUBLICATIONS

Chinese language office action dated Mar. 28, 2024, issued in application No. CN 202011347379.5.
Translation of office action dated Mar. 28, 2024.

* cited by examiner

CONTOURING SYSTEM

CROSS REFERENCE TO RELATED APPLICATIONS

This Application claims priority of Taiwan Patent Application No. 109138746, filed on Nov. 6, 2020, the entirety of which is incorporated by reference herein.

BACKGROUND OF THE INVENTION

Field of the Invention

The present invention relates to a contouring system, and, in particular, to a contouring system which uses a three-dimensional (3D) anatomical image as input for contouring volumetric targets that correspond to specific organs and/or tumors.

Description of the Related Art

Radiotherapy is an essential curative treatment for cancer, especially for head and neck cancer, which is the sixth most common cancer worldwide (Ferlay et al., *International Journal of Cancer*, 2019). However, its efficacy and safety heavily rely on the accurate contouring of volumetric targets, where the targets indicate tumors, multiple surrounding organs at risk (OARs), or any area requiring irradiation.

In clinical practice, the contouring task is the most time-consuming procedure and requires physicians to manually delineate the target contours on each of two-dimensional (2D) medical images of a 3D image, such as a series of 2D high-resolution Computer Tomography (CT) images. This task has been reported to take a physician up to four hours on a patient (Vorwerk et al., *Strahlentherapie und Onkologie*, 2014), potentially resulting in a delay to initiate a treatment and an impediment to implement an adaptive treatment. Furthermore, there are significant interobserver variability in the contouring and delineation of the different OARs (Mukesh et al., *The British Institute of Radiology*, 2012; Brouwer et al., *Radiation Oncology*, 2012)

Hence, this invention addresses the need to develop an automated contouring system for accurately contouring volumetric targets in a 3D image of a patient in order to reduce delays and the physician workload.

BRIEF SUMMARY OF THE INVENTION

To address the need described above, this disclosure provides an example of a contouring system that performs a neural network-based contouring method to automatically contour preset targets in a patient's 3D medical image, wherein the preset targets may be tumors and/or OARs and/or any area requiring irradiation. The contouring system includes a storage unit and a processing unit. The processing unit is configured to obtain a 3D image stored in a multi-dimensional image file format from the storage unit, and execute a contouring method to generate one or more contouring images of one or more preset targets. The contouring method executed by the processing unit includes the following steps. An image preprocessing module enhances image features of the one or more preset targets by applying at least one window setting. The image preprocessing module may improve the contouring accuracy by normalizing the scale of image intensity to an interval between 0 and 1; or by standardizing the distribution of image intensity to a mean of 0 and a standard deviation of 1. A neural network-based contouring module extracts a plurality of image representations of the one or more preset targets from the preprocessed images. The neural network-based contouring module then generates one or more contouring images corresponding to the one or more preset targets by decoding the image representations to the contouring images with their original resolution. The contouring images are binary images with an image intensity of zero or one. The image intensity of zero represents a background, while an image intensity of one represents a preset target which is contoured.

Accordingly, the contouring system implemented by the disclosed contouring method can perform a series of feature extractions in a 3D image, and thereby automatically contour one or more preset targets in the 3D image, wherein the preset targets may be a tumor and/or one or more OARs. Collectively, the contouring system of the present application may be applied to the contouring task of a treatment planning procedure to improve the efficiency of the contouring task.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is a preferred embodiment of the invention, which is intended to describe the basic spirit of the invention, but is not intended to limit the invention. The actual inventive content must be referenced to the scope of the following claims.

It must be understood that the terms "including" and "comprising" used in the specification are used to indicate the existence of specific technical features, numerical values, methodological steps, process operations, elements and/or components, but do not exclude additional technical features, numerical values, methodological steps, process operations, elements, components, or any combination of the above.

Ordinal terms used in the claims, such as "first," "second," "third," etc., are used to modify the elements appearing in the claims, and do not imply any prioritization, precedence relation, or a component is higher than the other component, or the chronological order in which the methodological steps are performed. The intention is to make a distinction between elements with the same name.

Figure 1A:
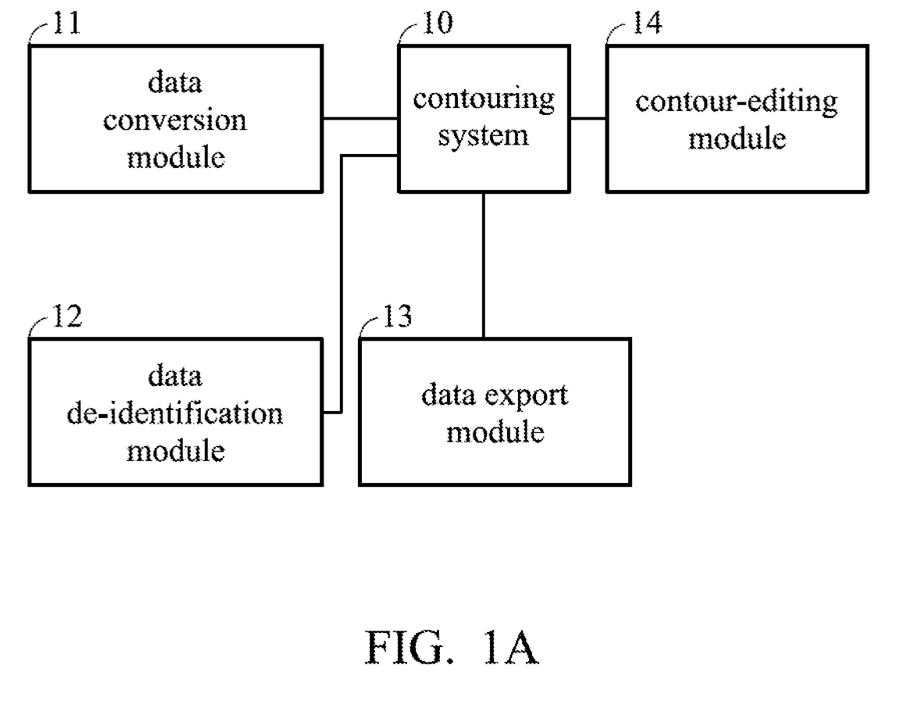
FIG. 1A is a block diagram of a contouring system with a plurality of expansion modules, according to an embodiment of the present application.
Figure 1B:
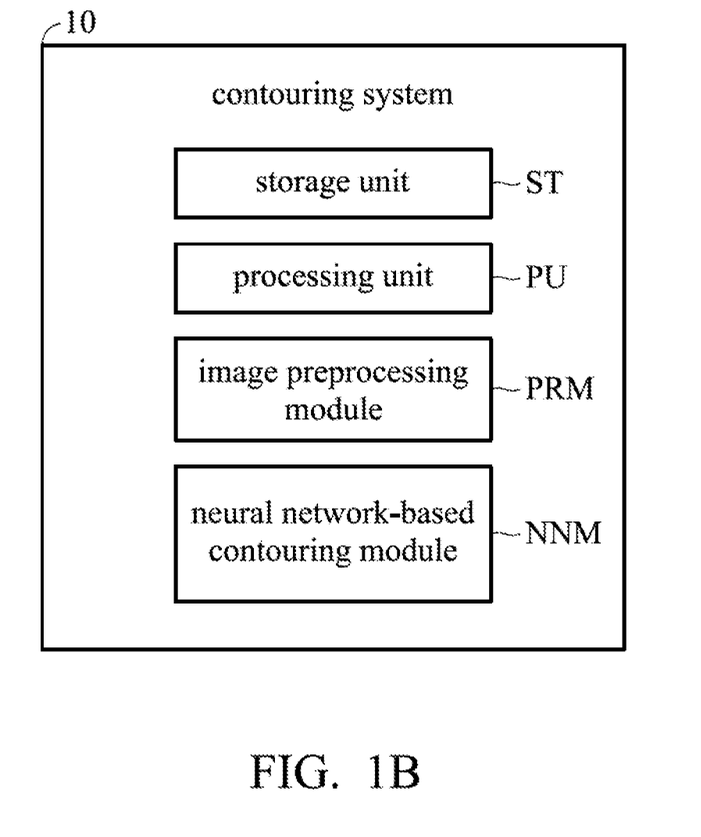
FIG. 1B is a block diagram of the contouring system, according to an embodiment of the present application.
Figure 2:
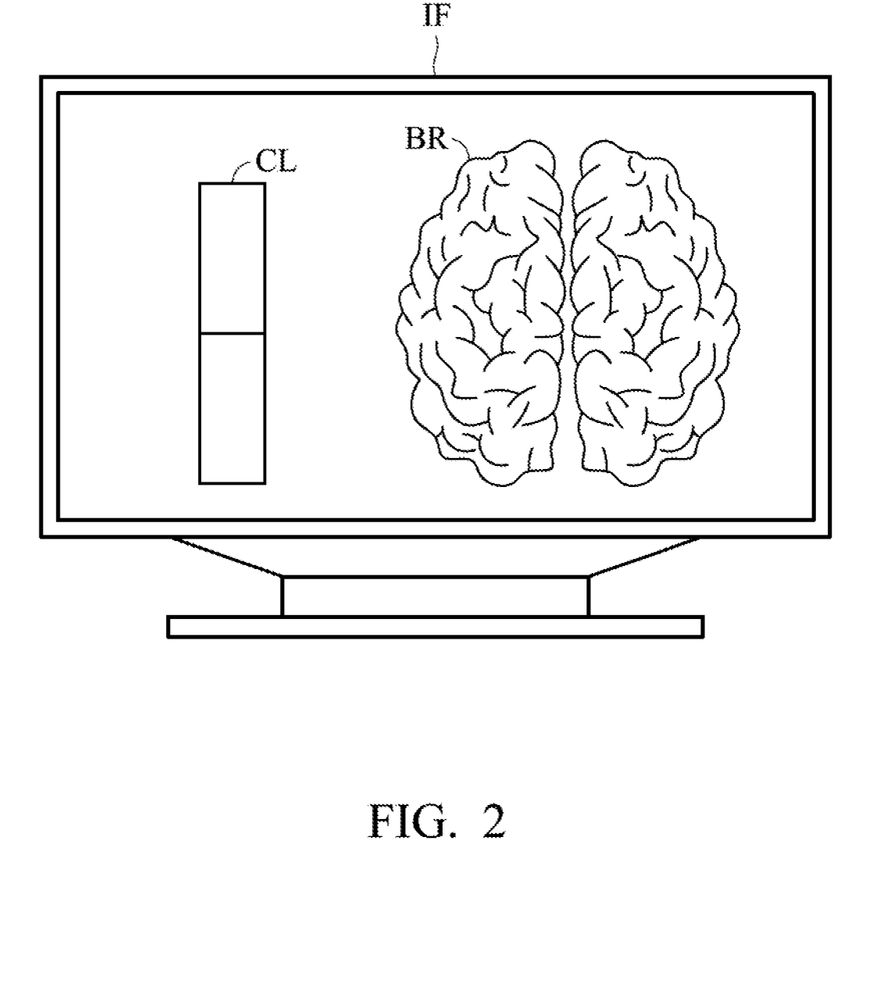
FIG. 2 illustrates an exemplary graphical user interface IF of the contour-editing module, according to an embodiment of the present application.
Figure 3:
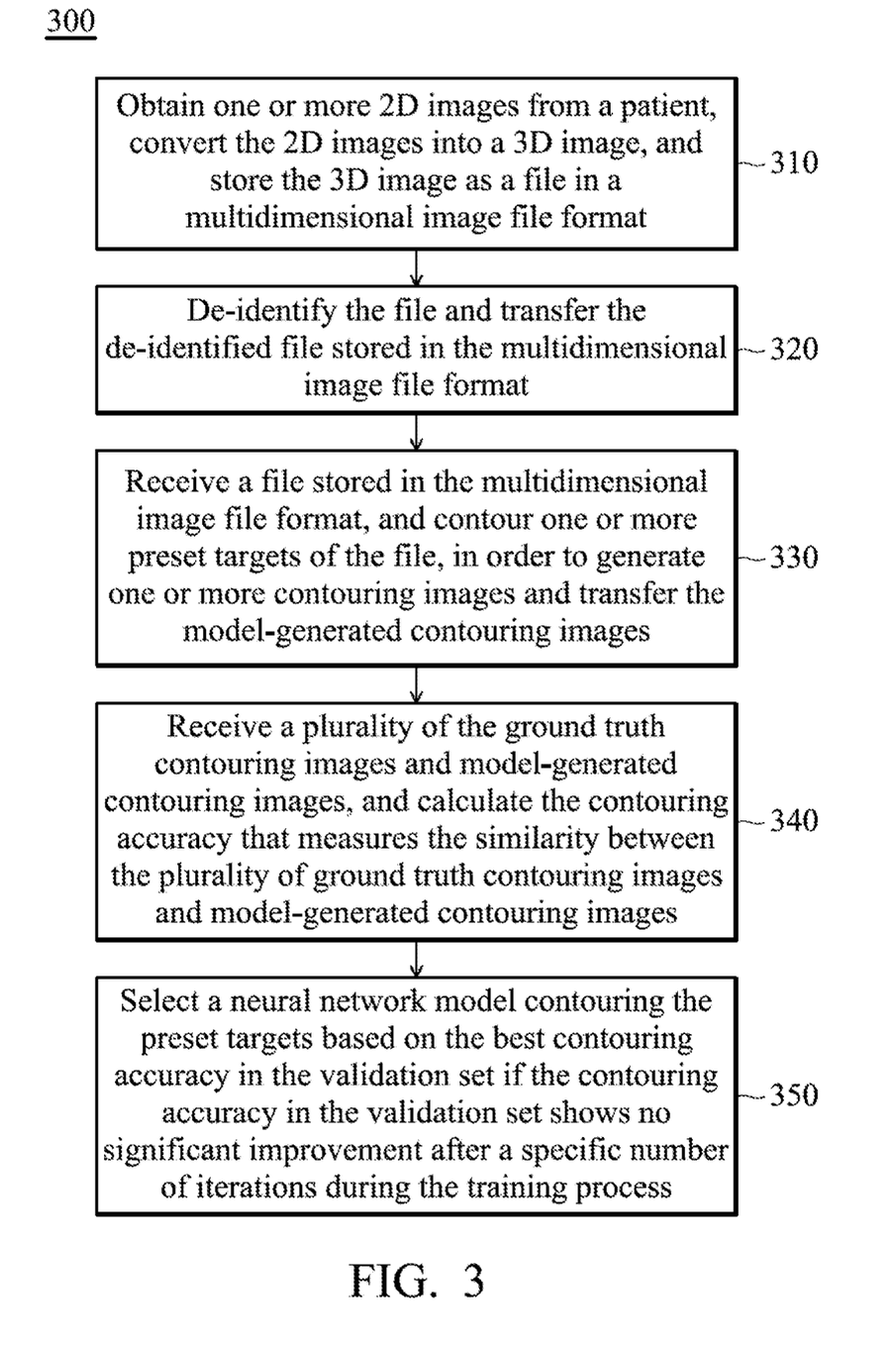
FIG. 3 is a flow diagram of a contouring method, according to an embodiment of the present application.

Please refer to FIG. 1A, FIG. 1B, FIG. 2, and FIG. 3. FIG. 1A is a block diagram of a contouring system 10 with a plurality of expansion modules comprising a data conversion module 11, a data de-identification module 12, a data export module 13, and a contour-editing module 14, according to an embodiment of the present application. FIG. 1B is a block diagram of the contouring system 10, according to an embodiment of the present application. FIG. 2 illustrates an exemplary graphical user interface IF of the contour-editing module 14, according to an embodiment of the present application. FIG. 3 is a flow diagram of a contouring method 300, according to an embodiment of the present application.

As shown in FIG. 1A, the contouring system 10 is coupled to a plurality of expansion modules comprising a data conversion module 11, a data de-identification module 12, a data export module 13, and a contour-editing module 14. The data conversion module 11, the data de-identification module 12, the data export module 13, and the contour-editing module 14 may be implemented individually or together by an integrated circuit, such as a microcontroller, a microprocessor, a digital signal processor, a central processor, a graphics processor, an application-specific integrated circuit (ASIC), a field-programmable gate array (FPGA), or a logic circuit. In an embodiment, the data conversion module 11, the data de-identification module 12, the data export module 13, and the contour-editing module 14 may be implemented by a device having the functionality of computation, transmission, and storage, without being limited to implementation by the device of the contouring system 10.

As shown in FIG. 1B, the contouring system 10 includes a storage unit ST, a processing unit PU, an image preprocessing module PRM, and a neural network-based contouring module NNM. In an embodiment, the contouring system 10 may be a computer, a server, or any other electronic device with the computation and storage functionality. In an embodiment, the contouring system 10 includes but is not limited to a storage unit ST and a processing unit PU.

In an embodiment, the storage unit ST may be implemented by a read-only memory, a flash memory, a floppy disk, a hard disk, an optical disk, a flash drive, a tape, a network-accessible database, or any storage media with the same functionality that is known by those skilled in the art. In an embodiment, the storage unit ST is configured to store a plurality of modules that are computer operable, one or more medical images received from a patient, a 3D image generated by the data conversion module 11, a de-identified 3D image generated by the data de-identification module 12, a file in a file format supported by a treatment planning apparatus and generated by the data export module 13, and a 3D image generated by the contour-editing module 14.

In an embodiment, the processing unit PU may be implemented by an integrated circuit, such as a microcontroller, a microprocessor, a digital signal processor, a central processor, a graphics processor, an ASIC, an FPGA, or a logic circuit.

In an embodiment, the image preprocessing module PRM and neural network-based contouring module NNM may be implemented by an integrated circuit, such as a microcontroller, a microprocessor, a digital signal processor, a central processor, a graphics processor, an ASIC, an FPGA, or a logic circuit. In an embodiment, the image preprocessing module PRM and neural network-based contouring module NNM may be implemented by software, firmware, or hardware.

In an embodiment, the contouring system 10 is applied to contour at least one preset target. The preset target may be a part of human anatomy, such as organs at risk (OAR) like the temporal lobe, the inner ear, the optic nerve, the optic chiasm, the pituitary gland, the lens, the eyeball, the pharynx, the larynx, the oral cavity, the parotid gland, the submandibular gland, the thyroid, the pharyngeal constrictor and the prostate, or the preset target may be an area requiring irradiation, such as the lymphatic drainage of the neck, abnormal gross lymph nodes, the tumors, etc.

In an embodiment, as shown in FIG. 2, the contour-editing module 14 includes a graphical user interface IF. The graphical user interface IF may display a plurality of columns CL, 3D images, and contouring images of the preset targets BR. The graphical user interface IF may be implemented by a monitor or a touch panel. The monitor or the touch panel may be a device included in the contour-editing module 14, an extended display presenting the contour-editing module 14, or an extended touch panel presenting the contour-editing module 14.

In an embodiment, the contouring system 10 with the modules 11-14 in FIG. 1A is applied to increase the efficiency of a contouring task during radiation treatment planning and reduce the physician workload. A contouring method 300 may be implemented by the contouring system 10 with the modules 11-14, as shown in FIG. 1A.

In an embodiment, in step 310, the processing unit PU obtains one or more 2D images from a patient. The data conversion module 11 converts the 2D images into a 3D image and stores the 3D image as a file in a multidimensional image file format.

In an embodiment, the processing unit PU is configured to access the 3D image in the multidimensional image file format stored in the storage unit ST.

In an embodiment, the 2D images of the preset target may be acquired by an imaging device, such as a computed tomography (CT) device. The 2D images are CT images that follow a Digital Imaging and Communication in Medicine (DICOM) standard. The DICOM images include a metadata and a pixel data.

In an embodiment, at least one preset target may be acquired by a CT device for capturing at least one 2D image of the at least one preset target. By the data conversion module 11, the at least one 2D image is converted into a 3D image, and the 3D image is stored as a file in the multidimensional image file format. The file in multidimensional image file format includes a header data and an image data. The header data is part of the metadata in the DICOM image.

In an embodiment, the processing unit PU obtains a 3D image stored in the multidimensional image file format and executes a contouring method to generate one or more contouring images of the one or more preset targets. In an embodiment, the image preprocessing module PRM enhances the image features of the one or more preset targets by applying at least one window setting. The image preprocessing module PRM improves the contouring accuracy by normalizing the scale of image intensity to an interval between 0 and 1, or by standardizing the distribution of image intensity to a mean of 0 and a standard deviation of 1.

In an embodiment, the data conversion module 11 converts the received 2D images into a file in a multidimensional image file format. The multidimensional image file format includes a common multidimensional image file format, such as a Neuroimaging Informatics Technology Initiative (NIfTI) file format or a Nearly Raw Raster Data (NRRD) file format. Specifically, the data conversion module 11 converts the received at least one 2D image into a 3D image, and then stores the 3D image as a file in the multidimensional image file format. The 2D image may be stored in a common image file format, such as the portable network graphics (PNG) file format or the DICOM file format.

In an embodiment, in step 310, the processing unit PU may process one or more medical images, such as the acquired CT images. The at least one preset target presented in the one or more acquired CT images may be a part of the human anatomy, such as OARs including but not limited to the temporal lobe, inner ear, optic nerve, optic chiasm, pituitary gland, lens, eyeball, pharynx, larynx, oral cavity, parotid gland, submandibular gland, thyroid, pharyngeal constrictor, and prostate, or the preset target may be an area requiring irradiation, such as the lymphatic drainage of the neck, abnormal gross lymph nodes, tumors, etc.

In an embodiment, one or more 2D images of at least one preset target are acquired by a magnetic resonance imaging (MRI) device. In step 310, the processing unit PU receives one or more 2D images, and the anatomical coverage presented in the 2D images may be an OAR or an area requiring irradiation. The OAR is a healthy organ that is adjacent to tumors and might be damaged during radiation. Hence, the key to improving patient outcomes for treatment planning is to focus the radiation dose on the tumors accurately and to avoid the radiation dose applied on the OAR.

In an embodiment, in step 310, the processing unit PU may process medical images stored in accordance with the DICOM file format. The main purpose of the processing unit PU is to store, access, and manage the medical images by processing and uploading the medical images to the Internet. DICOM images may be groups of a plurality of attributes and a pixel data. The attributes may include the summary of basic information, such as the patient's name, patient ID, examination-related information, image modality, imaging parameters, etc. The attributes facilitate the DIOCM images to be easily searched and reviewed. The pixel data depicts the intensity of each pixel in the image.

In an embodiment, CT images may be applied for capturing a 3D image of human anatomy, calculating the electron density based on CT numbers, and calculating the absorbed dose in tissue for radiation treatment planning, where the absorbed dose in tissue may be used for evaluating the quality of radiation treatment planning.

In an embodiment, the data conversion module 11 receives one or more 2D images of one or more preset targets, converts the 2D images into a 3D image, stores the 3D image in a multidimensional image file format, and transfers the image stored in the multidimensional image file format.

In an embodiment, the NIfTI format is a new image format. The multidimensional images can be stored as a single file by combining the attributes and the pixel data into one file.

In an embodiment, the data conversion module 11 converts one or more CT images in the DICOM file format (i.e., one or more 2D DICOM images) into an image in the NIfTI file format (i.e., 3D NIfTI image). The data conversion may be implemented using known kits such as dcm2nii, dcm2niix, dicom2nifti, or any other kits. When the data conversion module 11 converts one or more CT images in the DICOM format into an image in the NIfTI format, one or more 2D images are stacked and stored as a 3D image.

In step 320, the data de-identification module 12 may de-identify and transfer the file in the multidimensional image file format.

In an embodiment, the data de-identification module 12 transfers the file in the multidimensional image file format to a contour-editing module 14.

In an embodiment, the data de-identification module 12 executing a data de-identification method to retain an image resolution, an affine transformation matrix, and a numerical scale transformation of an image header of the multidimensional image, remove the patient's personal data from the image header of the multidimensional image, and store both image and the de-identified image header as another multidimensional image.

In an embodiment, the de-identification method executed by the data de-identification module 12 includes removing part of the image header, and storing the 3D images from which the part of the image header has been removed. In an embodiment, the de-identification method is to remove the patient's personal data that may exist in the image header of the multidimensional image when converting one or more 2D images into a 3D image. The multidimensional image's header includes image attributes and some basic information, such as the patient's name, patient's ID, and examination-related information.

In an embodiment, when the contouring system 10 and the data conversion module 11 are configured in different local area networks (LANs), data must be de-identified before the data transfer between the contouring system 10 and the data conversion module 11.

In an embodiment, when the contouring system 10 and the data conversion module 11 are configured in the same LAN (e.g., in the same hospital), either the raw data or the de-identified data can be selected for data transfer between the contouring system 10 and the data conversion module 11.

In step 330, the neural network-based contouring module NNM receives a file in the multidimensional image file format, and contours one or more preset targets of the file in the multidimensional image file format, in order to generate one or more contouring images and transfer the one or more contouring images.

In an embodiment, contour-editing module 14 is configured to provide functionalities for a medical domain professional to revise, select and confirm the result of automatically contouring (i.e., the contouring images which have been generated by the contouring module), and store the contouring images which has been revised, selected, and confirmed in the multidimensional image file format.

In an embodiment, in the neural network-based contouring module NNM, weights of a plurality of neural network layers are a plurality of pre-trained weights. The pre-trained weights are obtained by iteratively adjusting the weights during an accuracy-improving training process. The accuracy indicates a similarity between a plurality of ground truth contouring images and a plurality of contouring images that have been generated by the contouring module NNM. The ground truth contouring images are from an image database with the at least one preset target and are annotated by medical domain professionals, wherein the at least one preset target is a tumor, an organ at risk, or an area requiring irradiation.

In an embodiment, the neural network-based contouring module NNM performs a feature extraction process on the preprocessed 3D image to obtain a plurality of image representations, where the preprocessed 3D image is generated by the image preprocessing module PRM. The feature extraction process includes a plurality of convolution layers, a plurality of pooling layers, and a plurality of activation functions.

In an embodiment, in a feature extraction process, the neural network-based contouring module NNM extracts a plurality of image representations of at least one preset target in the 3D image that has been preprocessed. The NNM then generates contouring images of the preset target by decoding the image representations to the contouring images with their original resolution. The decoding process may include a plurality of operations, such as convolution, upsampling, and activation functions. The contouring images are binary images (with an image intensity of zero or one). An image intensity of zero represents a background, while an image intensity of one represents a preset target that is contoured.

In an embodiment, the contouring system 10 and the data conversion module 11 may be configured in a computer apparatus in either the same LAN or in different LANs. In an embodiment, when the contouring system 10 and the data conversion module 11 are configured in a computer apparatus in the same LAN, the contouring system 10 may receive a multidimensional image from the data conversion module 11 using either a local folder (i.e., the same computer apparatus) or an application program interface (i.e., different computer apparatus) which may be implemented through HyperText Transfer Protocol Application Programming Interface (HTTP API), and the contouring system 10 may execute a contouring method to generate contouring images corresponding to the preset targets. In another example, when the contouring system 10 and the data conversion module 11 are configured in different LANs, the contouring system 10 may receive a multidimensional image from the data conversion module 11 through the application program interface which may be implemented through HTTP API, and the contouring system 10 may use a contouring method to generate contouring images corresponding to the preset targets.

Figure 4A:
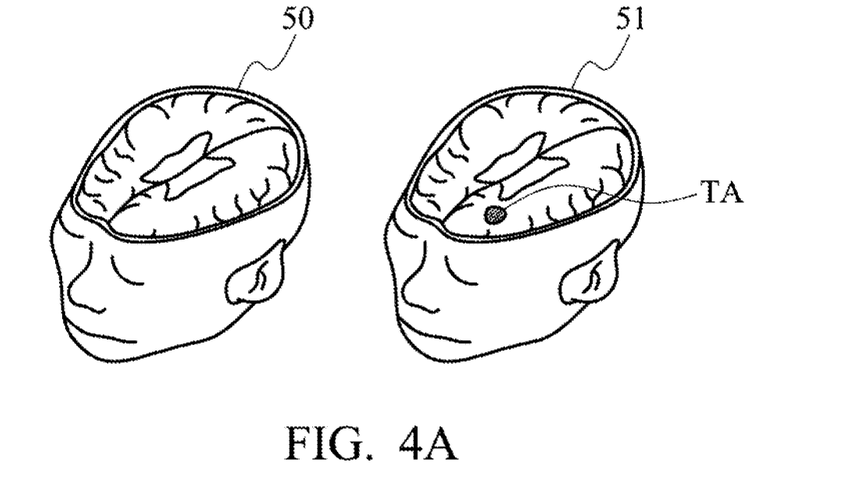
FIG. 4A illustrates an exemplary 3D head image with a contouring image of a tumor.
Figure 4B:
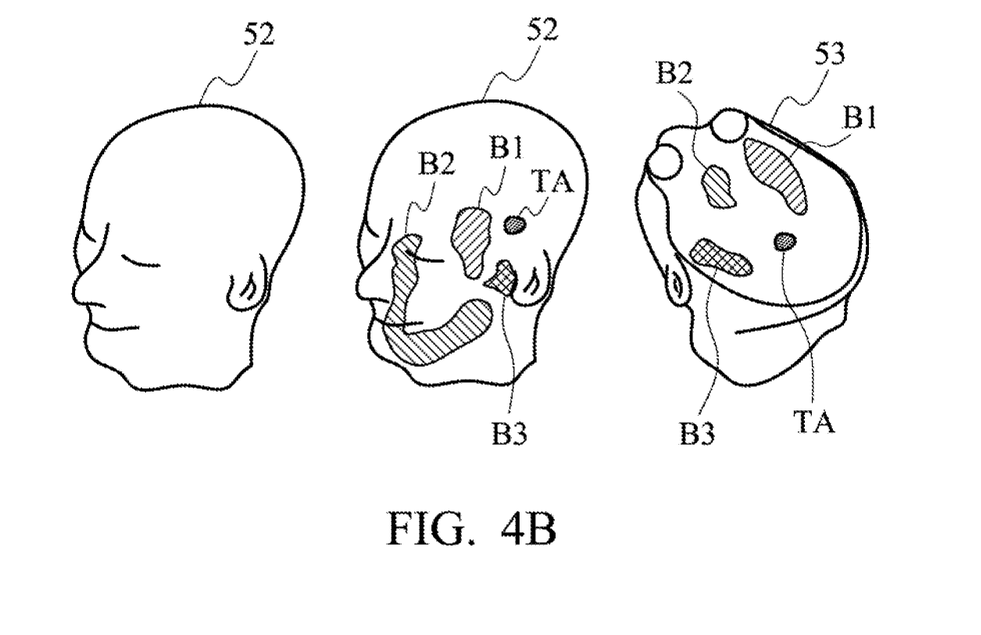
FIG. 4B illustrates another exemplary 3D head image with contouring images comprising a tumor and a plurality of OARs, according to an embodiment of the present application.

In an embodiment, please refer to FIG. 4A and FIG. 4B, which illustrate examples of one or more contouring images, according to an embodiment of the present application. The 3D image 50 with a preset target that has not yet been contoured. Assuming that the preset target is a tumor, the contouring system 10 contours the preset target tumor. The 3D image 51 with the contoured tumor TA is displayed by the contour-editing module 14.

In an embodiment, in the left panel of FIG. 4B, the 3D image 52 shows the preset target that has not yet been contoured. The preset targets of a tumor and OARs are contoured by the contouring system 10 and displayed by the contour-editing module 14. The contour-editing module 14 may be used to display and revise a plurality of the contoured preset targets. The contoured preset targets may be, for example, the tumor TA, the brain stem B1, the mandible B2 (part of which depicted in FIG. 4B is used as a representative), and the parotid gland B3. In the middle panel of FIG. 4B, the contour-editing module 14 displays the contoured preset targets of the brain stem B1, the mandible B2, the parotid gland B3, and the tumor TA, where the contoured preset targets of the 3D image 52 are contoured by the contouring system 10. The contour-editing module 14 may display part of the transverse section of the head anatomy, as shown in 3D image 53, for clearly presenting the contoured tumor TA (as shown in the right panel of FIG. 4B).

In an embodiment, the contouring system 10 adopts a neural network model.

In an embodiment, contouring system 10 adopts a neural network-based 3D segmentation algorithm, such as 3D U-net, 3D mask region-based convolutional neural network (3D Mask R-CNN), or 3D dilated multi-fiber network (3D DMFNet). The neural network model is generated by feeding both a plurality of 3D images and a plurality of ground truth contouring images corresponding to the 3D images to a neural network architecture, iteratively adjusting the weight of each neuron, gradually improving the contouring accuracy of a plurality of model-generated contouring images, and storing the weights with the highest contouring accuracy during an accuracy-improving training process.

In step 340, when training the neural network model, the contouring system 10 receives a plurality of ground truth contouring images and model-generated contouring images for a plurality of times and calculates the contouring accuracy of the plurality of ground truth and model-generated contouring images based on an accuracy evaluation metric. The ground truth contouring images are provided by radiation oncologists and used to train the neural network model and evaluate the model-generated contouring image. The model-generated contouring images are the contouring images generated by the neural network model.

In an embodiment, the purpose of the contour-editing module 14 provides the functionalities for a medical domain professional to revise, select and confirm the model-generated contouring images, and store the model-generated contouring images that have been revised, selected, and/or confirmed as a file in a variety of file formats.

In an embodiment, when training the neural network model, contouring system 10 may split the plurality of 3D images with the ground truth contouring images into three subsets comprising the training set, the validation set, and the testing set. The training set is used for training the network model. The validation set is used for selecting the optimum model that possesses the highest contouring accuracy of the model-generated contouring images during the training process. The testing set is used for testing the model accuracy when applied to a new dataset that is not used during the training process.

In an embodiment, the accuracy evaluation metric may be the Intersection over Union (IoU), volumetric Dice Similarity Coefficient (volumetric DSC), or surface Dice Similarity Coefficient (surface DSC). These metrics may range from 0 to 1. The greater the value, the higher the contouring accuracy.

For example, the IoU metric measures the intersection of the model-generated contouring image and ground truth contouring image divided by the union of the model-generated contouring image and ground truth contouring image.

For example, the volumetric DSC metric measures the double of the volume of the intersection of the model-generated contouring image and ground truth contouring image divided by the sum of volumes of the model-generated contouring image and ground truth contouring image.

For example, the surface DSC metric measures the sum of the acceptable surface areas of the model-generated contouring image and ground truth contouring image divided by a total surface area of the both contouring images. The acceptable surface is the model-generated surface (i.e. the surface of model-generated contouring image) that deviated from the ground truth surface (i.e. the surface of the ground truth contouring image) within a predefined acceptable tolerance (e.g., a 3-millimeter acceptable tolerance), where the acceptable tolerance is the distance between the model-generated surface and the ground truth surface.

In step 350, a neural network model of the preset target is built when the contouring accuracy of the model-generated contouring images in the validation set shows no significant improvement after a specific number of iterations during the training process.

In an embodiment, a model of a preset target (e.g., tumors) in the contouring system 10 is built (e.g., the model used for contouring tumors is built in the contouring system 10) when the contouring accuracy in the validation set shows no significant improvement after a specific number of iterations during the training process.

In an embodiment, the contour-editing module 14 may be used to revise, select, and confirm the model-generated contouring images, and transfer the confirmed contouring images to the data conversion module 11. The data conversion module 11 converts the confirmed contouring images into a file with target contouring items in a radiotherapy structure set (RTSS) file format, where the target contouring items are presented in the same amount as the confirmed contouring images, and stores the RTSS file into a storage unit in the data conversion module 11. In addition, an RTSS file format is a type of DICOM file format.

In an embodiment, the contouring image in a multidimensional image file format stores the volume of a structure (e.g., a tumor), whereas the contouring image in an RTSS file format stores a plurality of planner contours of a structure (e.g., a tumor).

In an embodiment, a CT device produces one or more 2D images of a preset target and stores as one or more DICOM images. DICOM is a standard that includes a file format definition and a network communication protocol for medical imaging. On the other hand, the RTSS file format is a widely adopted format for radiotherapy to store one or more sets of contour-based DICOM coordinates corresponding to the one or more contouring images. Accordingly, after data conversion module 11 converts one or more CT images in the DICOM file format into a 3D image in the NIfTI format, the 3D image is transferred to the contouring system 10. The contouring system 10 contours one or more preset targets and transfers the model-generated contouring images of the preset targets to the contour-editing module 14. The model-generated contouring images are received by the contour-editing module 14 and then revised and confirmed by radiation oncologists. The confirmed contouring images are transferred to the contouring system 10. The contouring system 10 transfers the confirmed contouring images to data conversion module 11. The data conversion module 11 converts the confirmed contouring images into the RTSS file, and stores the RTSS file in a storage unit of the data conversion module 11.

In an embodiment, the data conversion module 11 interfaces with other systems (e.g., the contour-editing module 14) using 3D images in the NIfTI format. However, 3D images in any file format may be supported by the data conversion module 11. An example of the NIfTI file format is used for demonstration. The present application is not limited to the NIfTI format for interfacing.

In an embodiment, the contour-editing module 14 may display the contouring images (e.g., tumors) through a graphical user interface IF, such as a monitor or a touch panel. Radiation oncologists may revise and confirm the model-generated contouring images using a mouse (when the graphical user interface IF is a monitor), a finger, or a stylus (when the graphical user interface IF is a touch panel). The contour-editing module 14 transfers the confirmed contouring images to the contouring system 10. The contouring system 10 transfers the confirmed contouring images to the data conversion module 11. The data conversion module 11 converts the contouring images into a file with target contouring items in an RTSS file format. The target contouring items are presented in the same amount as the confirmed contouring images and stores the RTSS file into a storage unit in the data conversion module 11.

In an embodiment, the storage unit of the data conversion module 11 is configured to provide a storage space, which may be implemented as read-only memory, flash memory, a floppy disk, a hard disk, an optical disk, a flash drive, a magnetic tape, a network-accessible database, or any storage media with the same functionality that is known by those skilled in the art.

Figure 5:
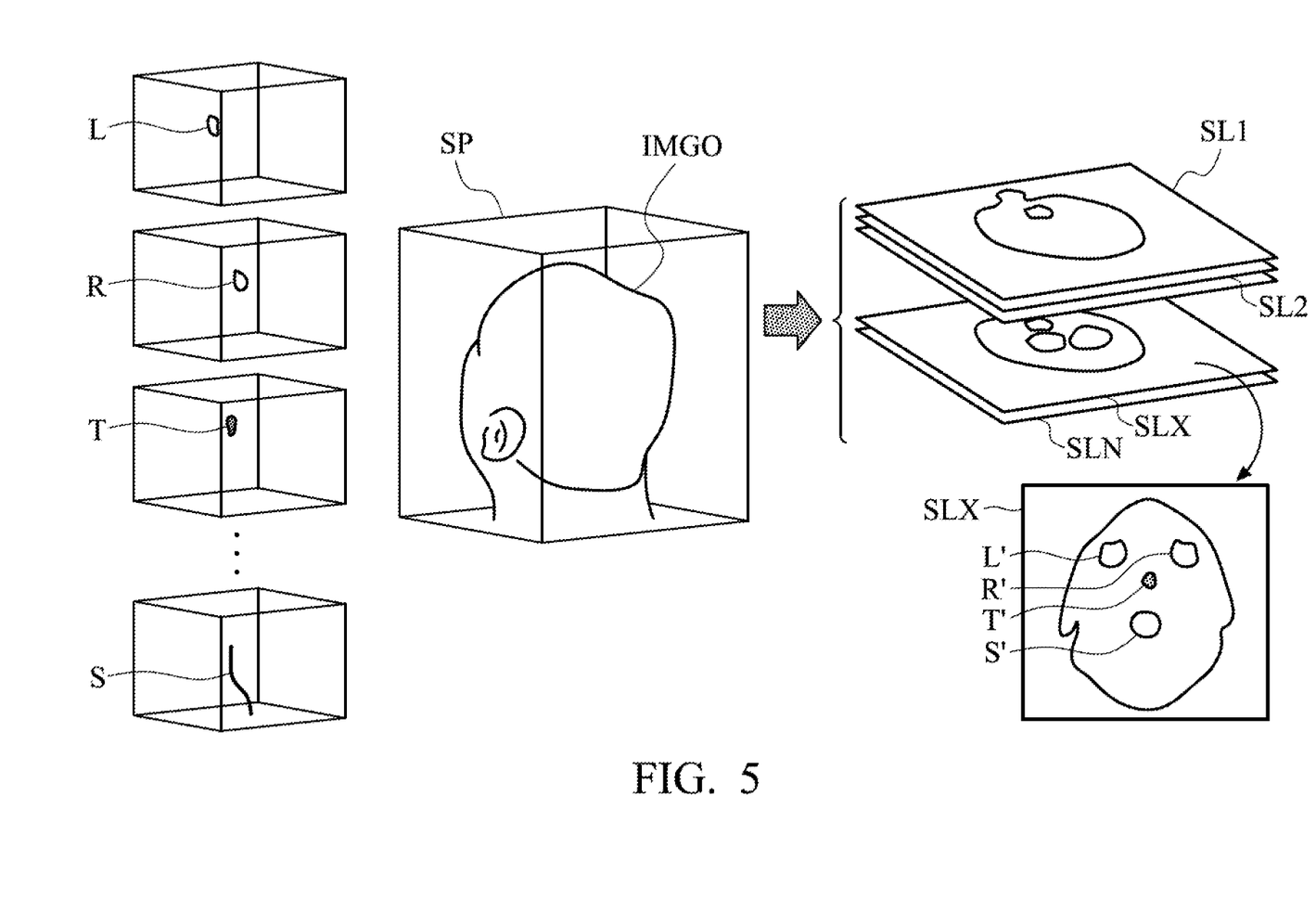
FIG. 5 illustrates a data export method that exports one or more contouring images to an RTSS file, according to an embodiment of the present application.

Please refer to FIG. 5, which illustrates a data export method that exports contouring images to an RTSS file, according to an embodiment of the present application.

The RTSS file is generated by way of extracting general attributes and specific attributes from one or more DICOM images of a patient. The one or more DICOM images of a patient may be acquired by a CT device or an MII device.

The general attribute is the general information regarding multiple DICOM images of a patient, such as information describing the patient, the manufacturer, and the modality. The general attribute may be filled in an information entity such as the patient, study, and series in the RTSS file.

The specific attribute means the unique information among multiple DICOM images of a patient such as an image number. The specific attribute may be filled in an information entity such as a structure set in the RTSS file.

The steps of exporting an RTSS file are as follows. First, the extracted general attributes and the specific attribute are filled in the RTSS file. Second, the target contouring items (e.g., OARs, tumors, areas requiring irradiation) corresponding to the contouring images are produced. The target contouring items may be, for example, the left parotid L, the right parotid R, the tumor T, and the spinal cord S. The target contouring item may include a set of contour-based coordinates in a coordinate space SP where a 3D image IMGO is located (e.g., a set of contour-based coordinates of the tumor T in the coordinate space SP). Moreover, each target contouring item includes information, such as an ordering number representing an OAR or a tumor, a unique identifier that identifies the DICOM image where the target contouring item is located, or the name of the target contouring item.

Finally, the sets of contour-based coordinates of OARs, tumors, or areas requiring irradiation in each of the DICOM images are produced respectively, based on the method of producing target contouring items introduced at the previous step. Accordingly, a contour may be composed of sets of multiple coordinates. For example, the topmost part of tumor T is depicted as 10 coordinates in CT image SL 1, the second topmost part of tumor T is depicted as 15 coordinates in CT image SL 2, and the bottommost part of tumor T is depicted as 5 coordinates in CT image SL 15. For example, the CT image SLX includes left parotid's contour L', right parotid's contour R', tumor's contour T', and spinal cord's contour S'.

In this example, one or more preset targets' contour of a volumetric anatomy may be integrated as a RTSS file. The one or more preset targets' contours may be represented by one or more target contouring items. On the basis of the coordinates specified in millimeters, the contours of each transverse image of the target contouring items are paired to the corresponding CT images SL1~SLN. In other words, the volumetric anatomy is represented by the multiple CT images SL1~SLN.

In another example, a data export module 13 is configured to export the file in the multidimensional image file format into that in a file format supported by a therapy planning apparatus. The data export method of data export module 13 is to extract the general attributes regarding multiple images and specific attributes regarding a single image from one or more DICOM images of a patient, to produce target contouring items corresponding to the contouring images of the preset targets, and to export sets of contour-based coordinates paired to the corresponding DICOM images of each target contouring item, in order for an imaging device (e.g., CT device) to reconstruct the spatial location of the preset targets.

Exporting the contouring images as an RTSS file that follows the DICOM standard reduces the required storage space because the RTSS file merely records the contour-based coordinates of the contouring images rather than the whole content of the contouring images. Accordingly, the RTSS file is widely adopted by most of the storage systems for medical imaging on the market. Therefore, the contouring images exported in an RTSS file may facilitate its further applications since it allows to be accessed by the storage systems for medical imaging.

Accordingly, the contouring system implemented by the disclosed contouring method can perform a series of feature extractions on a 3D image, and thereby automatically contour one or more preset targets in the 3D image, wherein the preset targets may be a tumor and/or one or more OARs. Collectively, the contouring system and the contouring method of the present application may be applied to the contouring task of a radiation treatment planning procedure to improve the efficiency of contouring a tumor, an OAR, and the area requiring irradiation.

What is claimed is:

1. A contouring system, comprising:
   a storage unit, configured to store one or more medical images of a patient; and
   a processing unit, configured to obtain a three-dimensional (3D) image stored in a multidimensional image file format from the storage unit, and execute a contouring method to generate one or more contouring images of one or more preset targets, wherein the processing unit executes the contouring method to:
   use an image preprocessing module to enhance image features of the one or more preset targets by applying at least one window setting, and to improve the contouring accuracy by normalizing the scale of image intensity to an interval between 0 and 1, or by standardizing the distribution of image intensity to a mean of 0 and standard deviation of 1;
   use a neural network-based contouring module to extract a plurality of image representations of the one or more preset targets from the preprocessed images, and then to generate one or more contouring images corresponding to the one or more preset targets by decoding the image representations to the contouring images with their original resolution, wherein the contouring images are binary images with an image intensity of zero or one, wherein the image intensity of zero represents a background while the image intensity of one represents the a preset target which is contoure;
   a data conversion module, configured to receive one or more two-dimensional (2D) images, convert the one or more 2D images into a 3D image, and store the 3D image as a file in the multidimensional image file format, wherein a file format of the one or more 2D image includes a common image file format or a multidimensional image file format, wherein the multidimensional image file format follows Digital Imaging and Communication in Medicine (DICOM) standard, wherein DICOM images include a metadata and a pixel data; and
   a data de-identification module, configured to retain an image resolution, an affine transformation matrix, and a numerical scale transformation of an image header in the multidimensional image file format and thereby remove the patient's personal data from the image header in the multidimensional image file format using a data de-identification method, and store both an image data and the de-identified image header as another image in the multidimensional image file format.

2. The contouring system as claimed in claim 1, wherein in the neural network-based contouring module, weights of a plurality of neural network layers are a plurality of pre-trained weights;
   wherein the pre-trained weights are obtained by iteratively adjusting the weights during an accuracy-improving training process, where the accuracy indicates a similarity between a plurality of ground truth contouring images and a plurality of contouring images which have been generated by the contouring module;
   wherein the ground truth contouring images are from an image database with the at least one preset target, wherein the ground truth contouring images are annotated by medical domain professionals, and the at least one preset target is a tumor, an organ at risk, or an area requiring irradiation.

3. The contouring system as claimed in claim 1, further comprising:
   a contour-editing module, configured to provide functions for a medical domain professional to revise, select, and confirm the contouring images which have been generated by the contouring module, and to store the confirmed contouring images which have been generated by the contouring module and confirmed by the medical domain professional in the multidimensional image file format.

4. The contouring system as claimed in claim 1, further comprising:
   a data export module, configured to export the contouring images in the multidimensional image file format as a file format supported by a treatment planning apparatus;
   wherein the data export module extracts general attributes regarding multiple images and specific attributes regarding a single image from one or more DICOM images of a patient, produces one or more target contouring items corresponding to the confirmed contouring images, and export one or more sets of contour-based DICOM coordinates corresponding to the one or more confirmed contouring images, in order for the treatment planning apparatus to reconstruct the spatial location of the one or more preset target.

5. The contouring system as claimed in claim 1, further comprising:
   a Computer Tomography (CT) device, configured to acquire the one or more 2D images of the at least one preset target, wherein the one or more 2D image are then pushed to the data conversion module for converting the one or more 2D image into a 3D image and storing the 3D image as the file in the multidimensional image file format.

6. The contouring system as claimed in claim 5, further comprising:
   a de-identification module, configured to de-identify the file in the multidimensional image file format.

7. The contouring system as claimed in claim 6, wherein the de-identification module transfers the de-identified file in the multidimensional image file format to a contour-editing module.

8. The contouring system as claimed in claim 1, further comprising:
   a data export module, configured to export the file in the multidimensional image file format into the file format following DICOM and supported by a treatment planning apparatus.

* * * * *